United States Patent [19]

Leitzke

[11] Patent Number: 5,302,298

[45] Date of Patent: Apr. 12, 1994

[54] PROCESS AND INSTALLATION FOR TREATING LIQUIDS CHARGED WITH POLLUTANTS

[75] Inventor: Ortwin Leitzke, Kaarst, Fed. Rep. of Germany

[73] Assignee: Wedeco Umwelttechnologien Wasser Boden Luft GmbH, Herford, Fed. Rep. of Germany

[21] Appl. No.: 778,141

[22] PCT Filed: Jun. 13, 1990

[86] PCT No.: PCT/DE90/00446

§ 371 Date: Dec. 13, 1991

§ 102(e) Date: Dec. 13, 1991

[87] PCT Pub. No.: WO90/15778

PCT Pub. Date: Dec. 27, 1990

[30] Foreign Application Priority Data

Jun. 19, 1989 [DE] Fed. Rep. of Germany ....... 3919885

[51] Int. Cl.$^5$ .............................................. C02F 1/78
[52] U.S. Cl. ................................... 210/748; 210/188; 210/192; 210/195.1; 210/197; 210/199; 210/201; 210/205; 210/760; 96/207; 261/DIG. 42
[58] Field of Search .................. 55/52, 53, 196, 199, 55/202; 261/21, 94, DIG. 42, DIG. 75; 210/188, 760, 748, 199, 201, 205, 195.1, 197, 192; 96/207

[56] References Cited

U.S. PATENT DOCUMENTS

| | | | |
|---|---|---|---|
| 3,855,124 | 12/1974 | Lapidot | 210/760 |
| 4,028,246 | 6/1977 | Lund et al. | 210/151 |
| 4,045,316 | 8/1977 | Legan | 204/158 |
| 4,141,830 | 2/1979 | Last | 210/63 Z |
| 4,167,973 | 9/1979 | Forte et al. | 210/760 |
| 4,179,616 | 12/1979 | Coviello et al. | 250/527 |
| 4,230,571 | 10/1980 | Dadd | 210/760 |
| 4,273,660 | 6/1981 | Beitzel | 210/760 |
| 4,352,740 | 10/1982 | Grader et al. | 210/760 |
| 4,548,716 | 10/1985 | Boeve | 210/652 |
| 4,595,498 | 6/1986 | Cohen et al. | 210/192 |
| 4,836,929 | 6/1989 | Baumann et al. | 210/760 |
| 4,913,827 | 4/1990 | Nebel | 210/748 |
| 4,942,594 | 7/1990 | Bertholdt et al. | 210/760 |
| 5,073,268 | 12/1991 | Saito et al. | 210/760 |
| 5,180,499 | 1/1993 | Hinson et al. | 210/760 |

FOREIGN PATENT DOCUMENTS

| | | |
|---|---|---|
| 0003879 | 9/1979 | European Pat. Off. |
| 0144952 | 6/1985 | European Pat. Off. |
| 0281940 | 9/1988 | European Pat. Off. |
| 2618338 | 11/1976 | Fed. Rep. of Germany |
| 2551622 | 6/1977 | Fed. Rep. of Germany |
| 2756400 | 6/1979 | Fed. Rep. of Germany |
| 3836850 | 5/1990 | Fed. Rep. of Germany |

OTHER PUBLICATIONS

Patent Abstracts of Japan, "Method for Treating Waste Liquid of Chemical Plating", Publication No. 01135587.
Patent Abstracts of Japan, vol. 12, No. 301, C-521, Aug. 16, 1988, application No. 61-217021.
Patent Abstracts of Japan, vol. 12, No. 56, C-477, Feb. 19, 1988, application No. 61-41638.
Fletcher, David B., "UV/ozone process treats toxics", *Waterworld News*, vol. 3, No. 3, May/Jun. 1987.
McGraw-Hill Publication, *Chemical Week*, "Groundwater treatment know-how comes of age".
Beaudet, B. et al., "Use of Advanced Oxidation Processes for Control of Color in Groundwater", Wasser Berlin '89 Apr. 10-16, pp. V-3-1-V-3-11.
Bollyky, L. Joseph, "Ozone in Water Treatment", vol. 1 Proceedings, Ninth Ozone World Congress, New York, 1989, pp. 720-742.
Lehr-und Handbuch der Abwassertechnik, pp. 470-471.
Gabel, B. et al., "Moglichkeiten der technischen Anwendung einer Kombination von Ultraviolette-Bestrahlung und $H_2O_2$-Behandlung Zur Desinfektion von Trinkwasser und Oxidation von Inhaltsstoffen", *Fachliche Berichte HWW$_2$* (1982), pp. 37-42.

*Primary Examiner*—Neil M. McCarthy
*Attorney, Agent, or Firm*—Kenyon & Kenyon

[57] ABSTRACT

A process and an installation for treating liquids, which are charged with pollutants that are difficult to break down, by means of wet oxidation with ozone-containing gas and UV radiation. The installation comprises injectors by means of which ozone-containing gas produced in an ozone generator can be passed into the liquid. The liquid is then introduced into a reaction and degasification vessel, before it passes through the UV irradiation units.

26 Claims, 3 Drawing Sheets

PROCESS AND INSTALLATION FOR TREATING LIQUIDS CHARGED WITH POLLUTANTS

BACKGROUND OF THE INVENTION

The invention relates to a process for treating liquids containing pollutants using ozone-containing gas and UV radiation as well as to an apparatus for carrying out the process.

The invention is directed first and foremost towards a process for treating liquids which are charged with pollutants that are difficult to oxidize. Chlorinated hydrocarbons, for example, belong to this substance group. Many of them are not biodegradable and some even have a toxic effect on organisms.

These substances can be saturated or unsaturated, aliphatic or aromatic hydrocarbons, in which some hydrogen atoms are substituted by halogens.

They can be low-molecular substances, for example the solvent trichloroethylene, or high-molecular lignins or humic acids.

Among these are compounds, which react slowly or not at all with ozone, one of the strongest oxidizing agents.

The compounds, which can hardly be broken up and which in this form cannot be attributed to the natural ecological cycle of elements and substances on our earth, are artificially and chemically synthesized to be used, for example, as propellants, coolants, solvents, pesticides and herbicides, or they are formed as by-products in some industrial processes, such as the chlorolignins formed in chlorine bleaching processes.

They seep out of garbage dumps and poison ground water and rivers. It is imperative to look for ways to detoxify these substances.

It is generally known that UV light is absorbed by some chemical compounds between the atoms in certain organic molecules and that it therefore loosens these compounds, so that they can be oxidized, that is broken up, by radicals.

Such oxidants for energetically excited compounds can be OH radicals. OH radicals can be formed by exposing aqueous solutions of hydrogen superoxide ($H_2O_2$) or ozone ($O_3$) to UV, in that the parent compounds $H_2O_2$ and $O_3$ also absorb UV light and split off oxygen atoms, which react with the water to form OH radicals.

Radical reactions with $H_2O_2$ and UV on organic compounds are generally known for water conditioning [applications] and have also been described (B. Gabel, B. Stachel and W. Thiemann, *Expert Reports HWW2*, pp. 37–42, 1982, "Möglichkeiten der technischen Anwendung einer Kombination von Ultraviolett-Bestrahlung und $H_2O_2$-Behandlung zur Desinfektion von Trinkwasser und Oxidation von Inhaltsstoffen" [Possibilities for the Technical Application of a Combination of Ultraviolet Radiation and $H_2O_2$ Treatment for Disinfecting Drinking Water and Oxidation of Components]).

In the same way, the process combinations, UV radiation and ozone, are also described (D. B. Fletcher, *Water World News*, vol. 3, no. 3, 1987, UV/Ozone Process Treat Toxics and K. Brooks, R. McGinty, *Chemical Week*, McGraw-Hill Publication, Ground Water Treatment Know-How Comes of Age and J. D. Zeff, E. Leitis, J. Barich, Ca., U.S., Ozone in Water Treatment, Vol. 1, *Proceedings, 9th Ozone World Congress*, New York, 1989, Uv Oxidation Case Studies on the Removal of Toxic Organic Compounds in Ground, Waste and Leachate Waters, pp. 720–731).

The Ultrox process (Ultrox = registered trademark of the firm Ultrox International, Santa Ana, Ca, V.St.v.A.) dealt with in these works has an UV-oxidant contact system for a continuous or a discontinuous liquid flow. The UV radiators are vertically mounted in a widely varying number in several chambers, which are arranged together in series. The water flows or is stagnant in these chambers and surrounds the lamps which are protected with quartz shield tubes. Ozone or other oxidants are fed into the chambers by means of jet diffusors.

The APO process (APO = registered trademark of the firm Ionization International, Dordrecht, Holland) (J.-A. Moser, M. Sc., ozone in Water Treatment, Vol. 1, *Proceedings, 9th Ozone World Congress*, New York, 1989, S. 732–742, The Treatment of Chlorinated Hydrocarbons at a High Concentration Level with a Photochemical Process) produces ozone with UV light of a short wavelength and enables the ozone to act in the water phase or in the gas phase on chlorinated hydrocarbons.

The problem with the $H_2O_2$-UV combination processes is that they do not achieve oxidation potentials that are as high as is possible with the $O_3$-UV combinations.

The previously known $O_3$-UV combination processes work with UV immersion radiators, such as Ultrox. These have large water-layer thicknesses in the radiation chambers, which are more difficult to penetrate with UV rays than is the case with continuous-flow radiators with thinner water layers. Moreover, in the case of these chambers, the ozone is fed directly with the carrier gas, whereby the ozone solution in the water is not optimal, and the gas bubbles of the gas which is not physically dissolved likewise have a disadvantageous effect for an UV-ray utilization.

The processes of generating ozone by means of UV rays, such as the APO process, or by means of electrolytic, anodic oxidation, produce ozone only in a small concentration, which is disadvantageous for the oxidizing capacity.

SUMMARY OF THE INVENTION

The object of the invention is to improve the effectiveness of the combined UV-ozone treatment.

This objective is solved in its process-related aspect by the invention as described herein.

It is achieved hereby that the liquid is supplied in a virtually bubble-free state with physically dissolved ozone to the UV radiation, through which means its effect is substantially intensified.

In accordance with the invention, it is recommended for the ozone-containing gas to be fed under increased pressure into the liquid and, to also increase the system pressure on the whole. This increases the ozone partial pressure in the liquid and also the solubility of the ozone, which promotes the effectiveness of the ozone treatment.

An important refinement of the invention consists in repeatedly treating the liquid in a circuit, whereby the liquid flow conducted in the circuit can be greater than the liquid flow that continuously runs in and runs off.

By this means, the most complete possible ozone absorption and a better UV transmission is achieved as a result of the dilution effect. Moreover, the UV light is repeatedly radiated in one and the same installation and the residence time in the irradiated area is prolonged.

The ozone-containing gas can be introduced into the inflow supply of the liquid to be treated or into a part of the inflow supply.

To increase the yield of the ozone brought into solution, it is recommended to permit the isolated, ozone carrier gas containing residual ozone to react with the liquid once more.

When technical oxygen is used to produce ozone and the ozone carrier gas is therefore oxygen, this oxygen can be supplied again, after being isolated from the ozone, via a drying system to the ozone source or to the ozone production.

A useful refinement consists in radiating with UV light of differing wavelengths, which can act at the same time or one after the other on a specific liquid volume. The wavelengths can thereby be discrete, for example the most used wavelength can be 254 nm and have other specific values, or they can also comprise a continuous wavelength range, alone or in any combination.

As a result of the difference in the wavelengths, the energy input can be adapted to the various reactions that take place with the pollutants.

The pH-value of the liquid to be treated can be regulated to increase its reactivity.

Accordingly, it is possible to heat the liquid to be treated in order to increase the reaction rate.

The refinement of the process enables only substances which are reactive with ozone, such as azo dyes, colloids and turbidities, to be destroyed or precipitated before the combined simultaneous effect of ozone and UV, so that the clarity of the liquid and thus the transmittance for the UV light and its effectiveness increase.

The device-related aspect of the invention is realized in by an installation in accordance with the invention.

The reaction and degasification vessel, in which on the one hand the reaction of the ozone with the pollutants and, on the other hand, the expulsion and isolation of the undissolved constituents of the ozone-containing gas takes place is constructed in the preferred specific embodiment according to the invention.

The liquid into which the ozone-containing gas has been introduced is conducted in a way which allows the mixture to initially attain the inner vessel. The gas which is not physically dissolved can escape out of this inner vessel and be removed at the discharge line. As a result of the feeding in the lower region of the inner vessel, the liquid rises in this vessel and flows over into the outer vessel. It is drained off from the stabilized zone in the lower region of the outer vessel.

Drainage lines, which lead back via a recycling line to the inflow supply, can be provided both for the draining liquid as well as for the circulating liquid.

This circuit, which enables one and the same liquid volume to be treated repeatedly, is an important design feature of the invention.

Another important design feature is the existence of several series-connected reaction and degasification vessels for intensifying the action.

In a preferred specific embodiment, the device for irradiating the liquid to be treated comprises an irradiation unit which is connected between the two reaction and degasification vessels.

However, an irradiation unit can also be arranged in the outlet line of the last reaction and degasification vessel and/or in the recycling line leading back from the outlet lines of the reaction and degasification vessels to the inflow supply.

To improve the yield of ozone brought into solution, the refinement can be provided.

The gas which is isolated in the first reaction and degasification vessel can still contain ozone constituents, which can still be put into effect with the measure, as indicated, in the second reaction and degasification vessel.

The ozone can be fed into the liquid by means of an inlet device arranged in the inflow supply of the liquid and/or by means of an inlet device arranged in the recycling line.

To intensify the UV influence, it is recommended to use UV-irradiation units of a constructive form that enables a flowing liquid layer of a relatively small thickness to be penetrated transversely by radiation.

It is beneficial to use those ozone generators which work with silent discharge because of the high yield.

BRIEF DESCRIPTION OF THE DRAWING

An exemplified embodiment of the invention is depicted in the drawing.

DETAILED DESCRIPTION OF THE INVENTION

Figure 1:
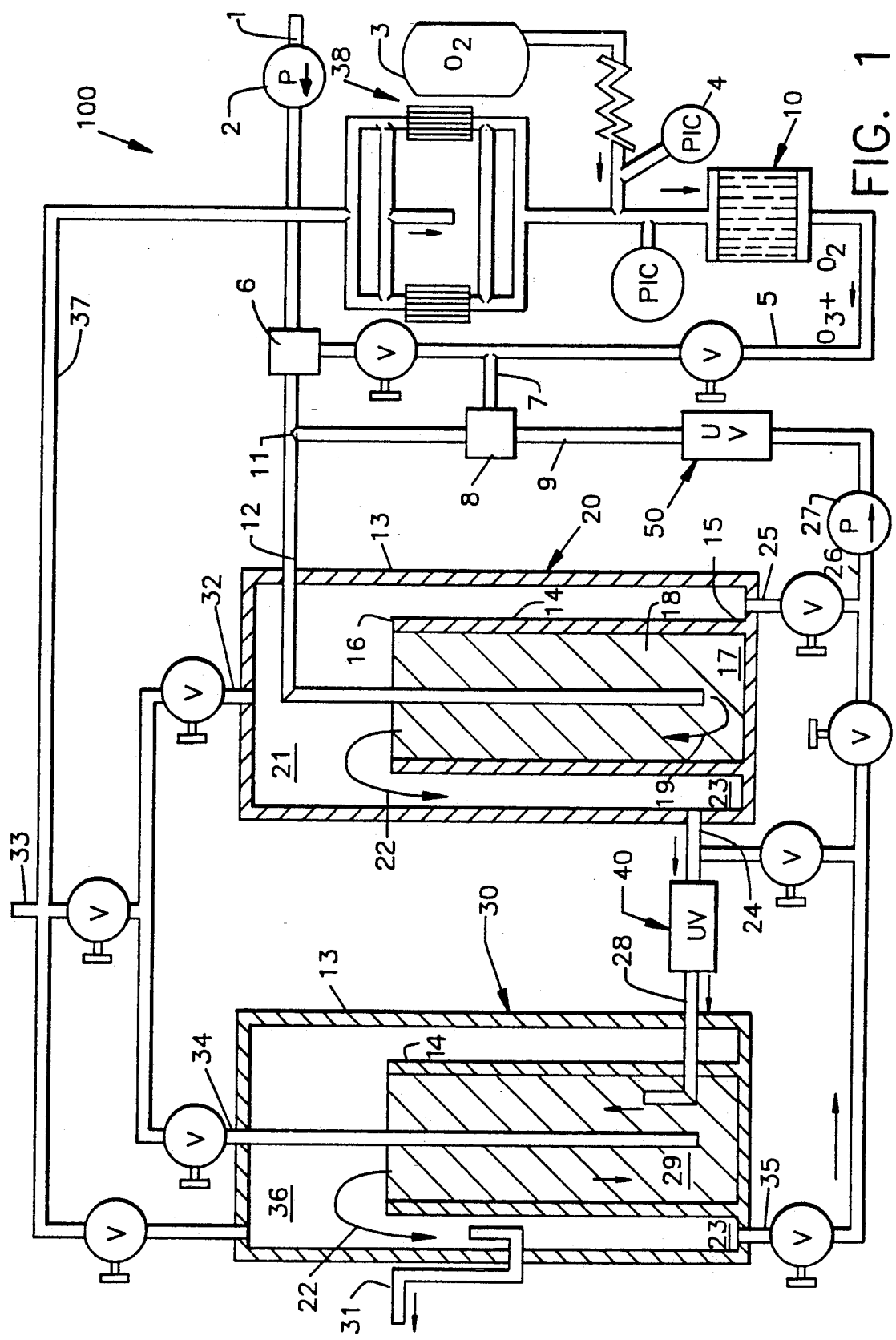
FIG. 1 through 3 show schematic diagrams of three installations for treating water charged with pollutants.

The installation denoted as a whole with 100 in FIG. 1 essentially comprises an ozone generator 10, a first reaction and degasification vessel 20, a second reaction and degasification vessel 30, an UV irradiation unit 40 and a second UV irradiation unit 50.

The untreated water which constitutes the liquid to be treated enters into the installation at the inflow supply 1 and is brought to an increased pressure of a few bar by means of a pump 2.

In the exemplified embodiment, the ozone is obtained from oxygen. The oxygen gas is tapped from a pressure tank 3 and sent via a pressure reducer 4 through the ozone generator 10, in which the ozone is produced in a concentration of about 100 g/m$^3$ oxygen. The oxygen-containing gas consisting of $O_3$ and $O_2$ is supplied via line 5 to the injector 6, which is arranged in the inflow supply 1 of the liquid. Thus, in the injector 6, the ozone-containing gas, which on its part is under a slightly increased pressure, is sucked into the liquid which is under an increased pressure.

Via a branch line 7, ozone-containing gas also attains the injector 8, which is arranged in a return line 9, which discharges at a location 11 downstream from the injector 6 into the inflow supply 1.

The liquid which has ozone-containing gas added to it by means of the injectors 6 and 8 arrives via the supply line 12 in the reaction and degasification vessel 20.

In the exemplified embodiment, the reaction and degasification vessel 20 consists of a cylindrical outer vessel 13, in which a cylindrical inner vessel 14 is arranged concentrically. At 15, the inner vessel 14 is tightly connected at the lower rim to the bottom of the outer vessel 13. The inner vessel 14 is open at the upper rim 16 and forms an overflow. The supply line 12 leads into the lower region 17 of the inner vessel 14, which is provided with fillings and/or baffle plates as indicated by the crisscross shading 18. Thus, the liquid flows in the direction of the arrow 19 through the vessel 14 to the top and is deflected several times turbulently, so that the ozone passed into the liquid has a chance to react, and a gas, which is only mixed, but not physically dissolved in the liquid, has a chance to be released and to rise up into the space 21 above the inner vessel. The liquid then flows over the upper rim 16 in the direction of the arrow 22 in the outer vessel to the bottom. In the lower region 23 of the outer vessel, there is a stabilization zone, in which the ozone reaction and the degasification reaction have already taken place for the most part. Outgoing lines 24 are situated in the lower region 23 on the outer vessel 13. Liquid flows over through these outgoing lines 24 into the UV irradiation unit 40, and 25, through which liquid flows over into line 26, in which a pump 27 is arranged, which again pressurizes the liquid. The liquid flows from the pump 27, across the UV irradiation unit 50, and through the return line 9, back to the injector 8.

The liquid components, which have passed through the UV irradiation unit 40, attain via the supply line 28 the lower region 29 of the second reaction and degasification vessel 30, which has exactly the same design in the exemplified embodiment as the reaction and degasification vessel 20. The liquid rises in the inner vessel of the reaction and degasification vessel 30, whereby the residual reaction takes place with the dissolved ozone. After flowing over the upper rim of the inner vessel 14, the ready-treated liquid arrives in the outflow 31. Another component of the liquid which has flowed over in the direction of the arrow 22 is, however, drawn off through the outgoing line 35 and arrives in the line 26 and once again crosses through the injector 8.

The ozone carrier gas containing the residual ozone isolated during the degasification in the reaction and degasification vessel 20 collects in the upper region 21 of the closed outer vessel 13 and is drawn off from there through the outlet line 32. This gas can either be blown off via line 33 or, however, be fed via a supply line 34 into the lower region 29 of the second reaction and degasification vessel 30, from where it rises in the liquid in the inner vessel 14, so that the residual ozone components once again have a chance to react.

The quantities of ozone carrier gas, which consists in the exemplified embodiment of oxygen, that collect in the upper region 36 can be recirculated via line 37 and a gas dryer 38 into the ozone generator 10. In place of oxygen, other gases such as air, nitrogen or argon can also serve as ozone carrier gases.

Figure 2:
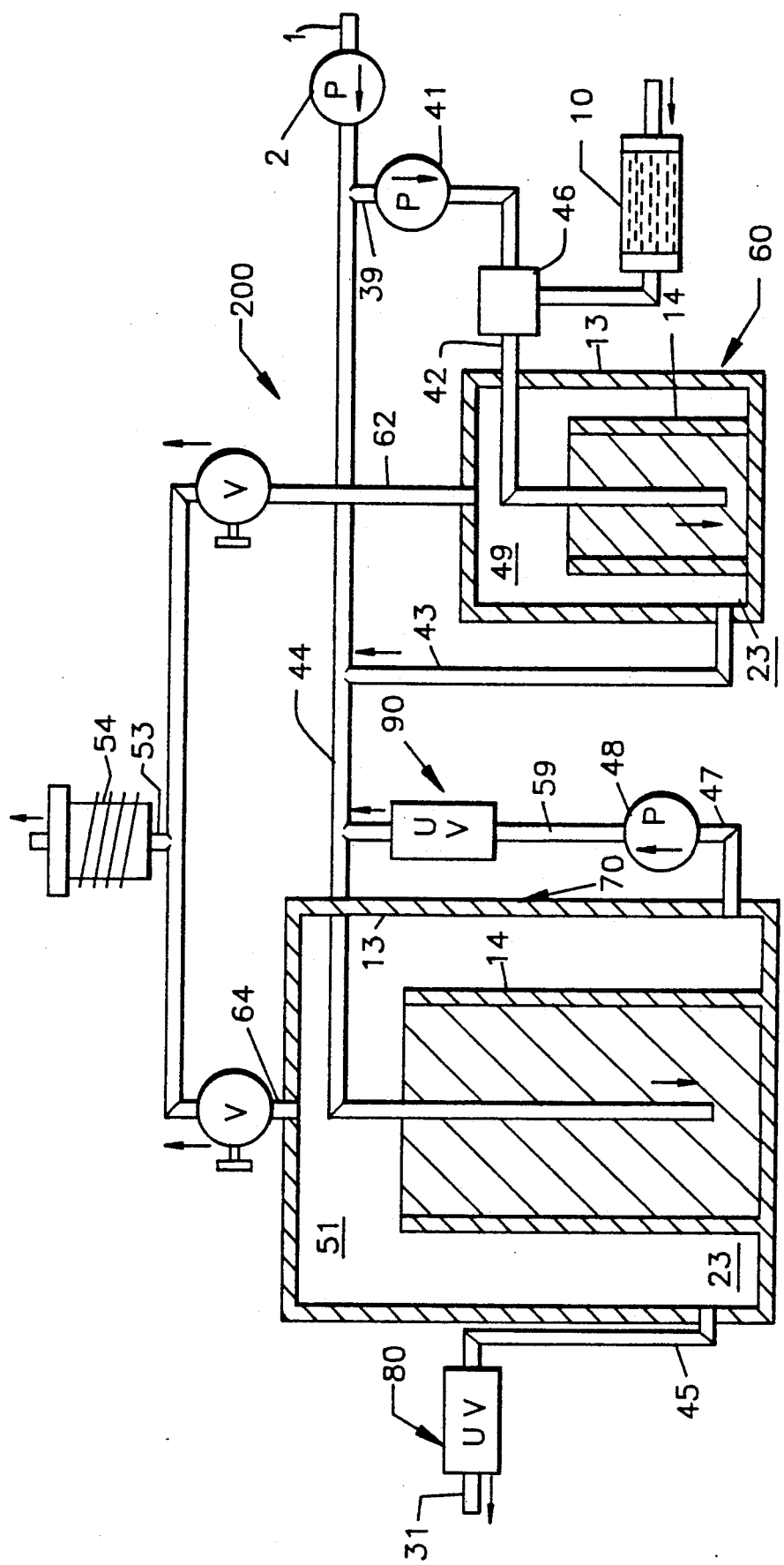
Figure 3:
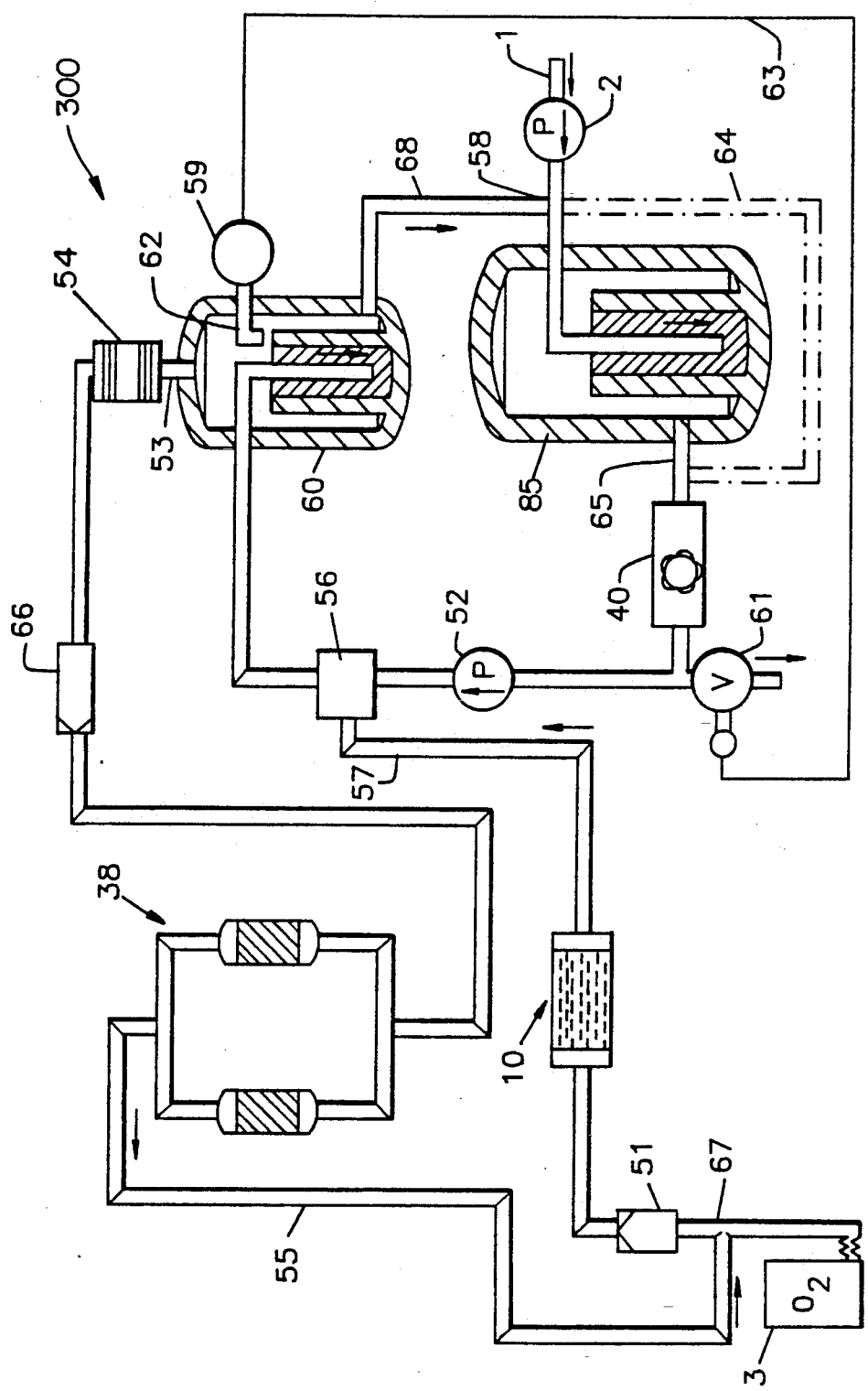

To the extent that the components provided in the specific embodiments 200 and 300 according to FIG. 2 or 3 correspond functionally, the reference symbols are the same.

The quantity of untreated water entering at the inflow supply 1 in the specific embodiment 200 of FIG. 2 and brought to system pressure by means of pump 2 is divided upstream from pump 2. The divided branch flow in line 39 is brought to a higher pressure by means of a booster pump 41 and is supplied through a line 42 to a reaction and degasification vessel 60, whose design and mode of operation essentially corresponds to the reaction and degasification vessel 20. Liquid from the lower region of the outer vessel 13 of the reaction and degasification vessel 60 is again admixed via line 43 with the main flow in line 44, which constitutes the supply line to a second reaction and degasification vessel 70, whose design and function correspond to the reaction and degasification vessel 20. After reacting with the ozone, liquid from the lower region 23 of the outer vessel 13 attains the outflow 31, whereby an UV irradiation unit 80 is arranged in the supply line 45 leading to the outflow 31. This UV irradiation unit 80 exposes the liquid to a final UV radiation.

Another line 47 leads out of the lower region 23 via a pump 48 and a line 59 to another UV irradiation unit 90, from where the liquid flows back to the main flow in line 44. The liquid with dissolved ozone is transferred several times by pumping via lines 47,44 in the circuit and is thereby repeatedly exposed to the UV radiation in the irradiation unit 90.

The ozone carrier gas which collects above the liquid in the regions 49 and 51 is let off via lines 62, 64 and 53 into the open air, after it has passed through a residual ozone converter 54.

In the specific embodiment 300 of FIG. 3, the liquid to be treated enters in the form of waste water via line 1 into the installation and is brought to pressure by means of pump 2. It flows through the reaction vessel 85 and, after that, the UV irradiation unit 40. It is subsequently brought to pressure again by another pump 52 and then passes through an injector 56, in which ozone-containing gas introduced via a line 57 is intermixed with the liquid. The liquid with the added ozone then arrives in the degasification vessel 60, where the gas component which contains residual ozone and has not been dissolved in the liquid is isolated and then drawn off via line 53. The liquid containing the dissolved ozone is fed via line 56 to point 58, where it is admixed with the untreated water that has been passed in. The ozone reaction begins in the reaction vessel 85, which is provided, when a large ionic-reaction component is needed to treat the untreated water in the particular case.

In certain cases, however, it is also possible to leave out the reaction vessel 85 and to proceed from point 58 via line 64 indicated by a dot-dash line to a point 65 behind the reaction vessel 85 and, from there, directly into the irradiation unit 40. After admixing the ozone in the injector 56, the degassing takes place in the degasification vessel 60, and the degassed liquid, which contains ozone only in a dissolved form, is again supplied via lines 56 and 64 to the UV irradiation unit 40. The liquid components provided with ozone thus pass through the UV irradiation unit 40 again only in a degassed form, which increases the effectiveness of the radiation.

The ozone is produced from oxygen which is stored in a pressure tank 3 and which attains the ozone generator 10 via a filter. The product of the ozone generator 10 is a mixture of remaining $O_3$ as a carrier gas and a few percent $O_3$. This mixture is supplied via line 57 to the injector 56.

The undissolved, residual-ozone-containing gas tapped from the degasification vessel 60 via line 53 is treated in the residual-ozone converter 54, in which the remaining ozone is reconverted into $O_2$. This is recirculated via a filter 66 and a gas dryer designated as a whole by 38 via line 55 to the location 67 in front of the filter 51 and is once again subjected to an ozonization in the ozone generator 10.

The quantity of liquid found in the installation can be kept constant by means of a level controller 59. This level controller 59 acts together with a level-sensing device 62 in the degasification vessel 60 and, by way of a control line 63, it triggers a valve 61, which discharges liquid when the level rises in the degasification vessel 60.

The construction of the irradiation units 40,50,80,90 enables them to be traversed by a relatively thin layer of the liquid flow and enables the UV light penetrating the liquid layer transversely to have negligible attenuation.

The installations attain their exceptional combined effectiveness of ozone and UV radiation in that ozone gas is carried in high concentrations and under pressure with the help of water-booster pumps and injectors into the liquid;

the solubility of the gas is not only increased by the rise in the ozone partial pressure (high ozone concentration and high system water pressure), but also by the rise in the water volume for feeding in the ozone with respect to the inflow of untreated water by recirculating the water several times and by means of baffle plates in the degasification and reaction tank;

by means of the first mentioned two points, bubble-free water, in which ozone has already been physically dissolved, is supplied to the UV radiation;

by increasing the amount of circulating water that is irradiated, with respect to the concentrated smaller untreated water flow, a dilution is achieved and the UV transmission is improved;

by means of the flow-through, UV irradiation apparatuses featuring positive radiation geometry and thin liquid water layers, the effect of the UV light on the liquid components and the dissolved ozone is good;

by means of the liquid circulation, it is possible to dose several times with UV light using one apparatus and to prolong the residence time in the irradiated region; and by passing in the ozone upstream from the degasification vessel and the beginning reaction of the ozone on the way to the point of application of the combined simultaneous effect of ozone and UV with the substances, such as dyes and turbidities, which are only ozone-reactive, the clarity of the liquid and thus the transmission of the UV light and the combined effect of ozone and UV increase.

Generally, substances which are difficult to break down and to a degree are even toxic can be oxidized by means of an ozone-UV combination to the extent that either the required limiting values are reached, or the substances can either be biodegraded further, or a mineralization even takes place when high enough doses are applied.

However, the process-related advantages of this invention compared to similar processes are:

there is no stripping of toxic substances as the result of the multiple forced conduction of gas;

a good ozone solubility factor as the result of several dissolving steps;

a supply of ozone-charged liquid, which is free of gas bubbles, for UV radiation;

a high UV-dose input through the repeated circulation of the liquid with an irradiation apparatus;

an increase in the UV transmission of the inflow liquid as the result of dilution and the possible reaction of the ozone with dyes;

installed combination possibility: to elevate the pH value to increase the temperature and flocculation through ozone possibility for varying the UV radiation spectrum using different radiation sources, by which means the radiation optimum can be adjusted to the absorption optimum of organic substances.

As already proven in the test, by combining this process with a biological step, values are attained which are less than the limiting values being discussed at the moment for the administrative regulation for drainage water runoffs of 500 $\mu$g per liter AOX per cbm waste by a power of ten, so that new technological standards are set.

What is claimed is:

1. A process for treating a liquid, which is charged with pollutants that are difficult to break down, by wet oxidation with an ozone-containing gas and UV radiation, comprising the steps of: passing and dissolving an ozone-containing carrier gas, without exposing the gas to UV radiation, into a liquid which is charged with pollutants, isolating undissolved carrier gas from the liquid containing ozone and removing gas bubbles from the ozonated liquid to render the ozonated liquid substantially free of gas bubbles, and thereafter irradiating the liquid containing ozone with UV radiation to achieve simultaneous radical formation and oxidation with radicals in the liquid.

2. The process according to claim 1, wherein the ozone-containing gas is fed under pressure greater than atmospheric pressure into the liquid.

3. The process according to claim 1, wherein the liquid is kept under pressure greater than atmospheric pressure during passing of the ozone-containing gas into the liquid and during isolating of the undissolved carrier gas.

4. The process according to claim 1, wherein the liquid is treated repeatedly by circulation in a circuit.

5. The process according to claim 1, wherein the ozone-containing gas is introduced into an inflow supply of the liquid to be treated.

6. The process according to claim 1, wherein the isolated, undissolved carrier gas contains residual ozone and wherein at least a portion of the isolated gas is passed into the ozonated liquid to attain a residual-ozone reaction.

7. The process according to claim 1, wherein the carrier gas is oxygen and wherein the ozone is produced from oxygen and wherein undissolved oxygen which is isolated from the liquid is dried and used to produce ozone.

8. The process according to claim 1, wherein the step of irradiating is conducted with UV light of a multiplicity of differing wavelengths.

9. The process according to claim 8, wherein a certain volume of the liquid is irradiated with the UV light of the differing wavelengths at the same time.

10. The process according to claim 8, wherein a certain volume of the liquid is irradiated with the UV light of the differing wavelengths one after the other.

11. The process according to claim 1, wherein the liquid charged with pollutants to be treated has a pH-value which is regulated to increase its ozone reactivity.

12. The process according to claim 1, wherein the liquid to be treated is heated so as to increase its reaction rate with ozone.

13. The process according to claim 1, wherein after the ozone-containing gas is introduced into the liquid and before the step of irradiating, the liquid is subjected to a flocculation filtration or a flocculation sedimentation.

14. An apparatus for treating a liquid which is charged with pollutants by oxidation with an ozone-containing carrier gas and UV radiation, comprising: a source of ozone-containing carrier gas, a device for introducing the ozone-containing gas into a liquid to be treated, a device for irradiating the liquid containing ozone with UV light, which is disposed downstream from the device for introducing the ozone-containing gas, and a reaction- and degasification-vessel system disposed between the device for introducing the ozone-containing gas and the irradiating device for removing substantially all gas bubbles from liquid ozonated by said introducing device prior to the ozonated liquid reaching the irradiation device.

15. The apparatus according to claim 14, wherein the reaction- and degasification-vessel system comprises a plurality of double vessels, each double vessel having an inner vessel disposed inside of an outer vessel, each outer vessel being closed and having an outlet line which lead from an upper region thereof for carrying non-dissolved carrier gas therefrom, each inner vessel being open at a top thereof to allow for an overflow of liquid, and each inner vessel receiving a supply line for the liquid containing ozone which feeds into a lower region of each inner vessel, and an outlet line for outflow of liquid emanating from a lower region of each outer vessel.

16. The apparatus according to claim 15, wherein each outer vessel has an outgoing line in a lower region thereof for outflow of a portion of liquid and recycling line for recirculating said portion of liquid to be treated again with ozone-containing gas by a second device for introducing ozone-containing gas.

17. The apparatus according to claim 14, wherein the reaction- and degasification-vessel system includes a first reaction and degasification vessel and a second reaction and degasification vessel arranged downstream from the first vessel, the second vessel having a supply line which is connected to an outgoing line of the first vessel.

18. The apparatus according to claim 17, wherein the device for irradiating the liquid to be treated comprises an irradiation unit which is connected between the first and second reaction and degasification vessels.

19. The apparatus according to claim 14 wherein the device for irradiating the liquid to be treated comprises an irradiation unit which is arranged in an outgoing line of the reaction and degasification vessel system.

20. The apparatus according to claim 14, wherein the device for irradiating the liquid to be treated includes an outgoing line from the reaction- and degasifications-vessel system and a recycling line which leads from the outgoing line into an inflow line of the liquid a second device for introducing an ozone containing gas.

21. The apparatus according to claim 15, further comprising a connecting line which leads from the outlet line of one reaction and degasification vessel into a lower region of an inner vessel of a subsequent downstream reaction and desgasification vessel.

22. The apparatus according to claim 14, wherein the device for introducing the ozone-containing gas into the liquid to be treated comprises a feed-in device arranged in an inflow supply line of the liquid.

23. The apparatus according to claim 14, wherein the device for introducing the ozone-containing gas into the liquid to be treated comprises a feed-in device arranged in a recycling line which leads back from an outgoing line of the reaction and degasification vessel system into an inflow supply line of the liquid.

24. The apparatus according to claim 14, wherein the source of ozone-containing gas comprises means for producing ozone by means of silent electric discharging out of oxygen-containing gas.

25. An apparatus for treating a liquid which is charged with pollutants by oxidation with an ozone-containing carrier gas and UV radiation, comprising: a source of ozone-containing carrier gas, a device for introducing the ozone-containing gas into a liquid to be treated, a device for irradiating the liquid containing ozone with UV light, which is disposed downstream from the device for introducing the ozone-containing gas, and a reaction- and degasification-vessel system disposed between the device for introducing the ozone-containing gas and the irradiating device wherein the reaction- and degasification-vessel system comprises a plurality of double vessels, each double vessel having an inner vessel disposed inside of an outer vessel, each outer vessel being closed and having an outlet line which leads from an upper region thereof for carrying non-dissolved carrier gas therefrom, each inner vessel being open at a top thereof to allow for an overflow of liquid, and each inner vessel receiving a supply line for the liquid containing ozone which feeds into a lower region of each inner vessel, and an outlet line for outflow of liquid emanating from a lower region of each outer vessel.

26. An apparatus for treating a liquid which is charged with pollutants by oxidation with an ozone-containing carrier gas and UV radiation, comprising: a source of ozone-containing carrier gas, a device for introducing the ozone-containing gas into a liquid to be treated, a device for irradiating the liquid containing ozone with UV light, which is disposed downstream from the device for introducing the ozone-containing gas, and a reaction- and degasification-vessel system disposed between the device for introducing the ozone-containing gas and the irradiating device, the reaction- and degasification-vessel system including a first reaction and degasification vessel and a second reaction and degasification vessel arranged downstream from the first vessel, the second vessel having a supply line which is connected to an outgoing line of the first vessel.

* * * * *

UNITED STATES PATENT AND TRADEMARK OFFICE
CERTIFICATE OF CORRECTION

PATENT NO. :     5,302,298
DATED      :     APRIL 12, 1994
INVENTOR(S) :    LEITZKE, ORTWIN

It is certified that error appears in the above-indentified patent and that said Letters Patent is hereby corrected as shown below:

Column 2, line 16, change "ozone" to -- Ozone --;

Column 2, line 16, change "Ozone in Water Treatment" to -- "Ozone in Water Treatment" --;

Column 2, lines 18-20, change "The Treatment of Chlorinated Hydrocarbons at a High Concentration Level with A Photochemical Process" to -- "The Treatment of Chlorinated Hydrocarbons at a High Concentration Level with A Photochemical Process" --;

Column 6, line 49, change "$O_3$" to --$O_2$--;

Column 9, line 25, change "and" to -- and a --;

Column 9, line 49, change "a" to -- to a --.

Signed and Sealed this

Twenty-second Day of October, 1996

Attest:

BRUCE LEHMAN

Attesting Officer    Commissioner of Patents and Trademarks